United States Patent [19]
Miller et al.

[11] Patent Number: 5,831,130
[45] Date of Patent: *Nov. 3, 1998

[54] CONDENSED PHASE PREPARATION OF 2,3-PENTANEDIONE

[75] Inventors: Dennis J. Miller, Okemos, Mich.; Scott M. Perry, Beaumont, Tex.; Paul T. Fanson, Stockbridge; James E. Jackson, Haslett, both of Mich.

[73] Assignee: Board of Trustees operating Michigan State University, East Lansing, Mich.

[ * ] Notice: The term of this patent shall not extend beyond the expiration date of Pat. No. 5,731,471.

[21] Appl. No.: 847,558

[22] Filed: Apr. 24, 1997

[51] Int. Cl.$^6$ .................................................. C07C 45/00
[52] U.S. Cl. ............................................... 568/397
[58] Field of Search ............................................. 568/397

[56] References Cited

U.S. PATENT DOCUMENTS 2,859,240  11/1958  Holmen et al. .
4,729,978  3/1988  Sawicki .

OTHER PUBLICATIONS

Wadley, Douglas C. et al, Lactic Acid Conversion to 2,3–Pentanedione and Acrylic Acid over . . . Journal of Catalysis 165, 162–171 (1997).

Gunter, Garry C., et al., FTIR and $^{31}$P–NMR Spectroscopic Analyses of Surface Species . . . Journal of Catalysis 164, 207–219 (1996).

Gunter, et al., Journal of Catalysis 148, 252–260 (Jun.–Jul. 1994).

Gunter, et al., Ind.–Eng. Chem. 34:974–980 (1995).

Biomass conference 1298–1304 (Aug. 30–Sep. 2, 1993).

Proc. 14th North American Meeting of Catalysis Society (Jun. 1993).

AIChE Meeting (Nov. 1994).

Corn Utilization Conference (Jun. 1994).

AIChE (Fall 1992).

Corn Utilization Conference (1992).

Primary Examiner—Gary Geist
Assistant Examiner—Jafar Parson
Attorney, Agent, or Firm—Ian C. McLeod

[57] ABSTRACT

A condensed phase process for the preparation of purified 2,3-pentanedione from lactic acid and an alkali metal lactate is described. The process uses elevated temperatures between about 200° to 360° C. for heating a reaction mixture of lactic acid and an alkali metal lactate to produce the 2,3-pentanedione in a reaction vessel. The 2,3-pentanedione produced is vaporized from the reaction vessel and condensed with water.

21 Claims, 5 Drawing Sheets

CONDENSED PHASE PREPARATION OF 2,3-PENTANEDIONE

GOVERNMENT RIGHTS

This invention was funded by Department of Energy Grant # DE-FC05-920R22072. The U.S. Government has certain rights in this invention.

BACKGROUND OF THE INVENTION (1) Summary of the Invention

The present invention relates to a condensed phase process for the preparation of 2,3-pentanedione by reacting lactic acid and an alkali metal lactate in a reaction vessel in an aqueous solution at elevated temperatures above about 200° to about 360° C. and then removing volatilized 2,3-pentanedione and water from the reaction vessel. In particular, the present invention relates to a process which produces the 2,3-pentanedione in relatively high yield.

(2) Description of Related Art

Lactic acid (2-hydroxypropanoic acid) is a bifunctional, optically active molecule traditionally used as a food additive and in textile production. It is produced by starch-based fermentation processes, and can have applications in biodegradable polylactide polymers.

2,3-Pentanedione is a high-value fine chemical currently produced in limited quantities ($\sim 4 \times 10^3$ kg/year) through a multistep chemical synthesis or by recovery from dairy waste. It is used primarily as a flavoring ingredient but has potential for applications as a feedstock, a solvent and as a photoinitiator for polymers.

Primary pathways of lactic acid chemical conversion are shown in FIG. 1. Direct dehydration of lactic acid to acrylic acid has long been of interest as a potential route to polymers from biomass, and most lactic acid conversion processes have focussed on this reaction. U.S. Pat. Nos. 2,859,240 to Holmen et al and 4,729,978 to Sawicki describe the formation of acrylic acid.

The vapor phase formation of 2,3-pentanedione from lactic acid over inorganic catalysts, particularly sodium salts and bases is described by some of the inventors herein in Gunter, et al., J. of Catalysis 148 252–260 (June–July 1994) and Gunter et al., Ind.-Eng. Chem. 34:974–980 (1995). These inventors herein discussed this conversion in a Biomass conference 1298–1304 (Aug. 30–Sep. 2, 1993). Other abstracts are: Proc. 14th North American Meeting of Catalysis Society (June 1993); AIChE Meeting (Nov. 1994); AIChE Meeting (Nov. 1994); Corn Utilization Conference (June 1994); 13th North Amer. Meeting of Catalysis Soc (May 1993); AIChE (Fall (1992); Corn Utilization Conference (1992); Proc. 12th Corn Utilization Conference, St. Louis, Mo. (June 1994). In these publications the 2,3-pentanedione was produced, but a separation process was not described. The best yields and selectivities (Table 2 of Gunter et al (1994) and Tables 1 to 4 of Gunter et al (1995)) were with sodium phosphate, sodium nitrate, sodium arsenate, sodium hydroxide, sodium hydrogen phosphate and all were too low to be economic. There was a need for yields which made the process economically viable. An additional problem was that there was a need for a separation step to remove the 2,3-pentanedione from the reactant lactic acid and numerous by-products of the reaction.

U.S. application Ser. No. 08/547,932, filed Oct. 25, 1995, describes an improved vapor phase process based upon the use of solid supports and catalysts wherein the 2,3-pentanedione is separated from water. Inorganic cesium salts are preferred. This vapor phase process works well and is used commercially; however, it requires several process steps. There is a need for an improvement.

OBJECTS

It is therefore an object of the present invention to provide an improved process for the production of a purified 2,3-pentanedione from lactic acid. It is particularly an object of the present invention to provide a process which is relatively easy to perform, is economical and produces the 2,3-pentanedione in good overall yield and selectivity. These and other objects will become increasingly apparent by reference to the following description and the drawings.

DESCRIPTION OF PREFERRED EMBODIMENTS

Figure 1:
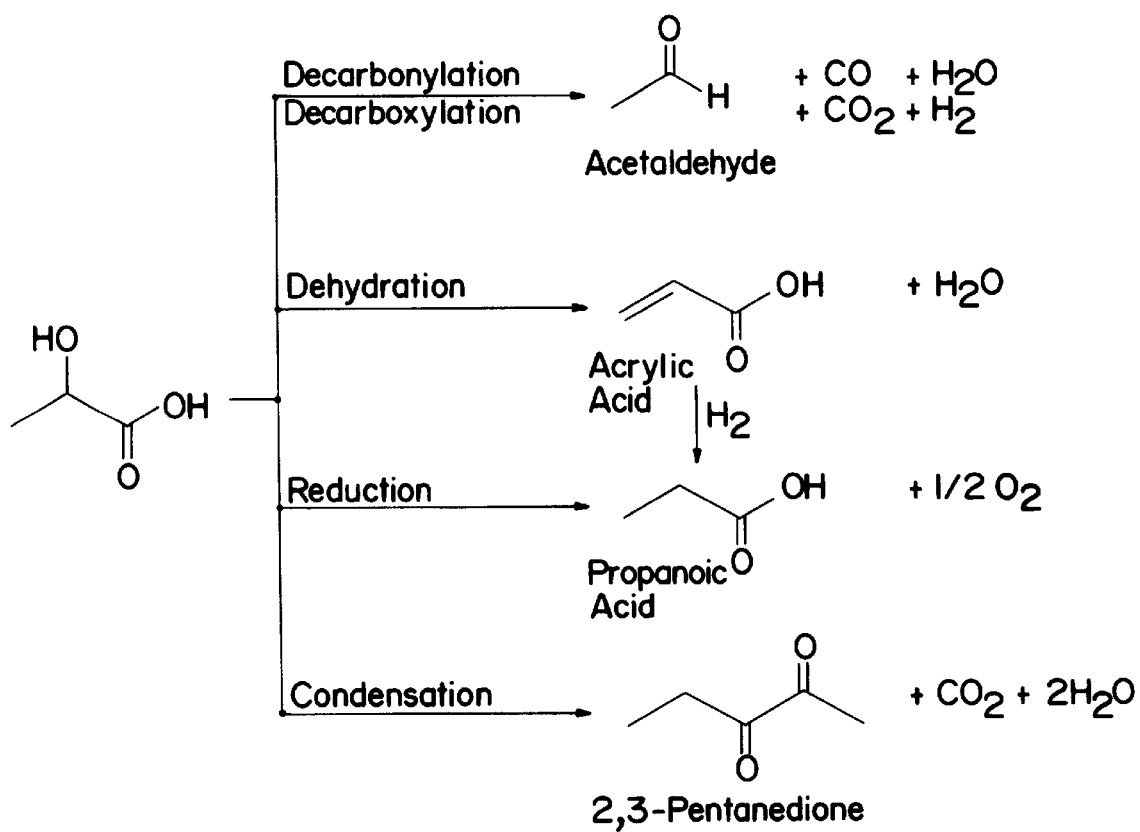
FIG. 1 is a schematic diagram showing various conversions of lactic acid described in the prior art, particularly a condensation reaction to 2,3-pentanedione, as well as the major by-products of the condensation to form 2,3-pentanedione.

The present invention relates to a process for the preparation of 2,3-pentanedione which comprises: providing in a reaction vessel a solution of water, an alkali metal lactate and lactic acid in a reaction mixture in the presence of a non-reactive gas; heating the reaction mixture in the reaction vessel to a temperature between about 200° and 360° C. to produce 2,3-pentanedione which volatilizes from the reaction mixture along with water; removing the 2,3-pentanedione with water from the reaction vessel; and optionally separating the water from the 2,3-pentanedione. The mole fraction of alkali metal lactate to lactic acid is preferably between 0.02 and 0.2, most preferably 0.05 to 0.07.

Most preferably sodium, potassium or cesium, alkali metal lactates or mixtures thereof are used in the process. Most preferred is cesium lactate.

The temperature of the reaction mixture is between about 200° C. and 360° C.; most preferably 230° to 260° C. with the temperature controller set at 280° to 300° C. The pressure is preferably atmospheric. Higher or lower pressures could be used so long as the reactants are liquid, but are not necessary.

The non-reactive gas is preferably helium. Other non-reactive gases include neon, argon, xenon and nitrogen. Steam is a non-reactive gas under the present conditions.

The lactic acid solution preferably contains more than about fifty (50) percent by weight lactic acid in water. Most preferably the aqueous solution contains between about 70 and 80 percent by weight lactic acid and the balance is water. Where a batch process is performed, higher amounts of lactic acid can be used up to the pure compound. The alkali metal lactate preferably contains less than 50% water. Preferably the reaction mixture contains a small amount of water at the reaction temperature to prevent the formation of oligomers. Usually the amount is less than 20% water.

The water is preferably separated from the 2,3-pentanedione and any other reaction products after removal from the reaction vessel. A solvent extraction with a non-water miscible solvent, to remove 2,3-pentanedione in the water can be performed. The azeotropic method of U.S. patent application Ser. No. 08/547,932, filed Oct. 25, 1995 can be used. This method distills the 2,3-pentanedione from the reaction mixture which is then condensed to separate the 2,3-pentanedione from the water.

Semi-batch or continuous processing can be used. The continuous process is preferred.

The condensed-phase conversion of lactic acid has the following advantages over vapor phase technologies:
1) 2,3-pentanedione is produced in a single reaction processing step in good yields at low cost.
2) Feed vaporization, which is a significant technical challenge in light of the properties of lactic acid, is avoided.
3) The reaction proceeds without use of supported inorganic catalysts, thereby facilitating uniform reaction, eliminating mass transport limitations, and minimizing difficulties associated with catalyst deactivation.
4) The reactions can be performed at lower temperatures and pressures than in the vapor phase process.
5) The need to remove all non-volatile fermentation residues from the feed lactic acid prior to conversion can be circumvented.

Figure 2:
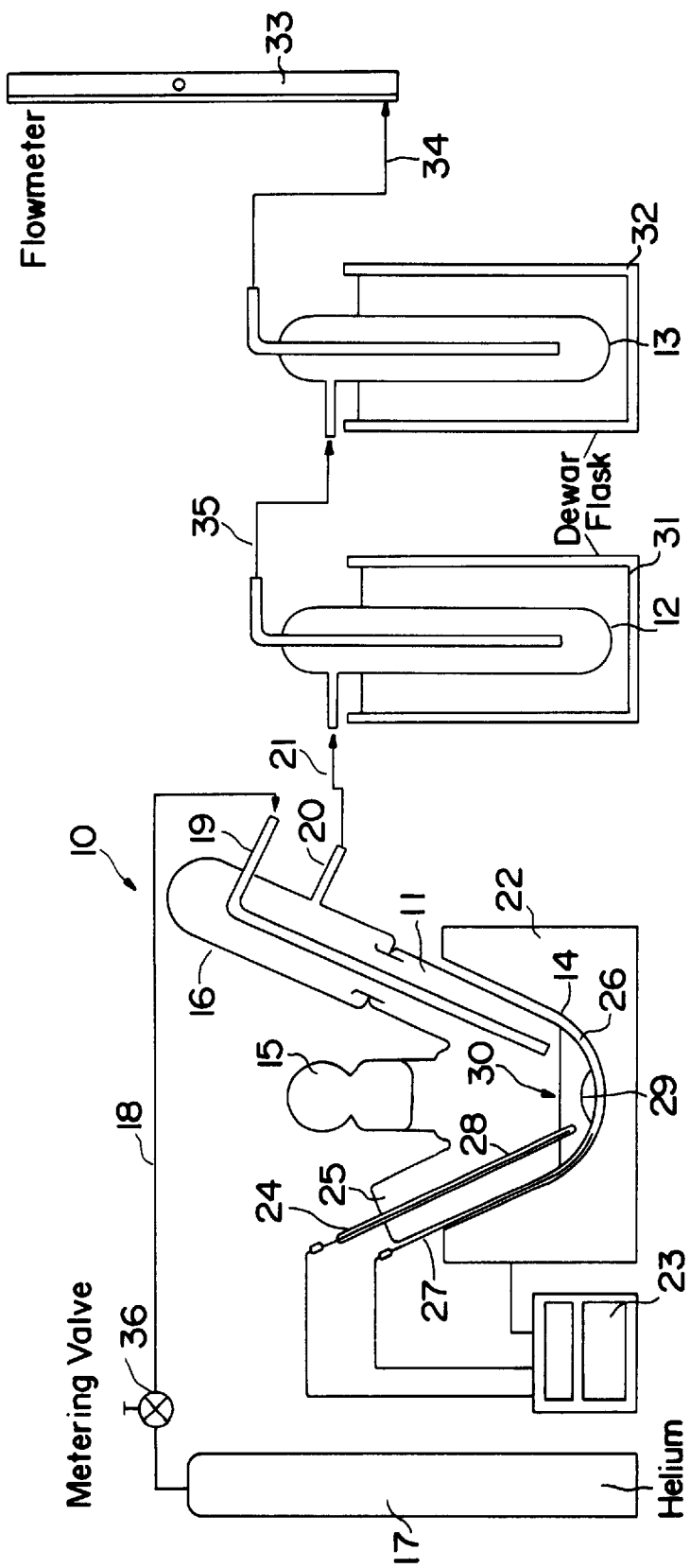
FIG. 2 is a schematic diagram showing a batch reactor apparatus 10 including a vessel 11 for a condensed phase conversion of lactic acid and an alkali metal lactate to 2,3-pentanedione and traps 12 and 13 for condensing and recovering the 2,3-pentanedione.

As shown in FIG. 2, semi-batch conversion of lactic acid to 2,3-pentanedione was accomplished in a glass reaction apparatus 10 consisting of a reaction vessel 11 and two product collection traps 12 and 13. The first trap 12 and the second trap 13 condense the 2,3-pentanedione and water. The reaction vessel 11 consisted of a 100 ml 3-neck round-bottomed flask with three 24/40 ground joints. For semi-batch operation, the vessel 11 was fitted with a thermocouple well 14, a ground glass stopper 15, and a distillation head 16. The distillation head 16 allowed continuous introduction of a carrier inert gas (He) from the tank 17 into the vessel 11, and continuous exit of the carrier gas and volatile products (e.g. 2,3-pentanedione and water) from the vessel 11. The carrier gas was introduced into and out of the reaction vessel 11 by tube 18 via a glass 6 mm ID inlet tube 19 and outlet tube 20 115 mm in length. Gases exiting the vessel 11 were routed through 6 mm ID PTFE tubing 21 to two cold-finger-type collection traps 12 and 13 in series. One trap 12 was maintained at 0° C. using ice, and the second trap 13 at 77° K. using liquid nitrogen. The vessel 11 was heated using a spherical heating mantle 22 connected to an OMEGA CN2011 (Stanford, Mass.) programmable temperature controller 24A. The control thermocouple 24 was placed in the 4 mm ID glass thermowell 25 fitted in a thermometer adapter 23. Several milliliters of high temperature melting bath oil 26 (Sigma; M-9389) were placed in the thermowell 25 to improve heat conductance. In addition to the control thermocouple 24, a thermocouple 27 was placed between the mantle 22 and the bottom of the reaction vessel 11 to monitor mantle 22 and vessel 11 wall temperatures. A magnetic stirrer 29 was provided in the reaction mixture 30.

The cold traps 12 and 13 were surrounded by Dewar flasks 31 and 32. The first trap 12 was cooled by ice (0° C.). The second trap 13 was cooled by liquid nitrogen (77° K.).

A gas flow meter 33 was connected to line 34 from the second trap 13. Traps 12 and 13 were connected by line 35.

A metering valve 36 was used to regulate the flow of the gaseous helium.

Figure 2A:
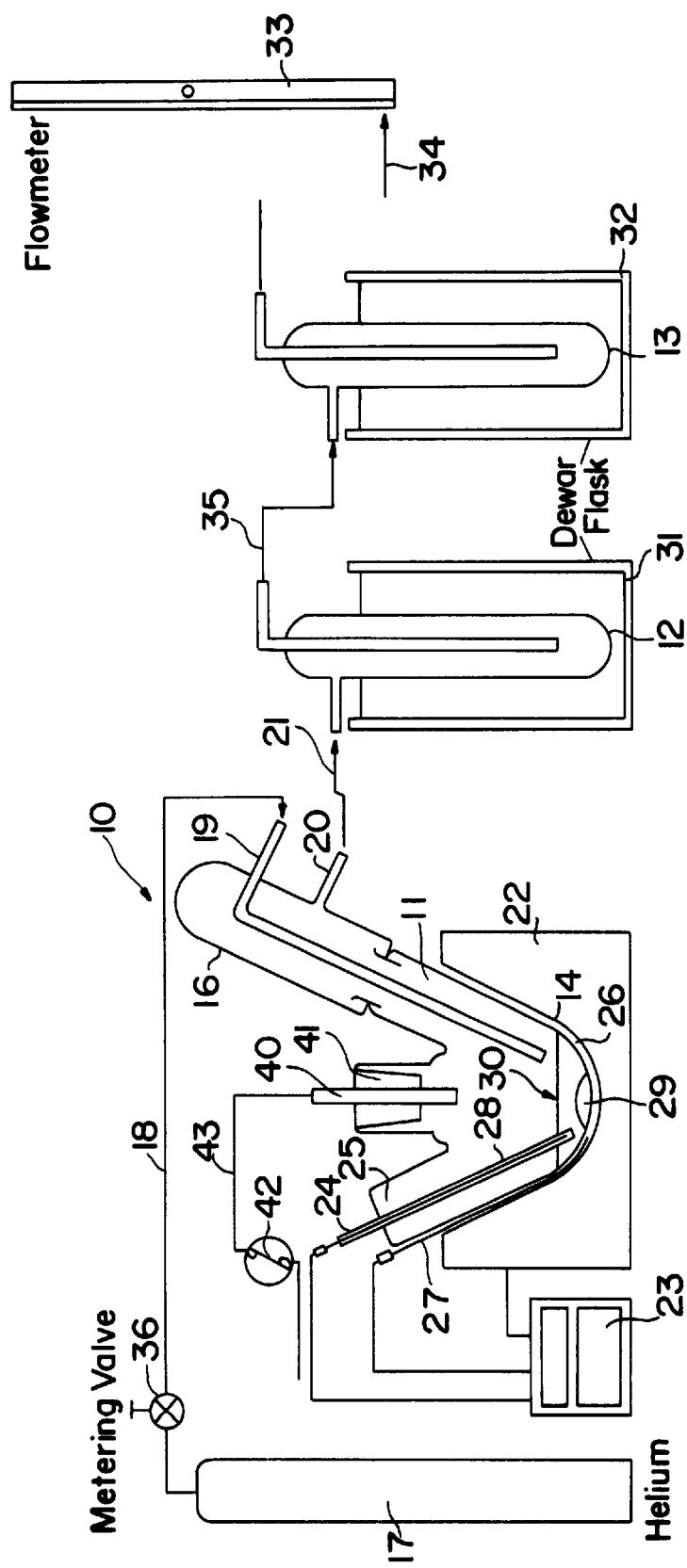
FIG. 2A shows modifications for a continuous reactor 10A.

Continuous condensed-phase conversion of lactic acid to 2,3-pentanedione was achieved using the semi-batch conversion apparatus 10 except that the ground glass stopper 15 was replaced with a 6 mm ID glass inlet feed tube 40 mounted by means of a 24/40 PTFE thermometer adapter 41 as shown in FIG. 2A. Lactic acid feed solution was introduced using a MASTER FLEX (Cole-Parmer, Chicago, Ill.) peristaltic pump 42 (model number 7518-10) and variable flow digital drive (model number 7524-10), connected by VITON 0.8 mm ID (6412-13) tubing 43 to the feed tube 40.

Various means can be used to prepare the alkali metal lactates. They can be purchased or made by a neutralization process. The alkali lactates used in condensed-phase conversion were preferably prepared by drop-wise addition of an 88 weight percent aqueous solution of food-grade lactic acid into a stoichiometric quantity of aqueous alkali base which produced the alkali metal lactate and water in equimolar amounts as a result of the reaction. The solution was mixed in an ice bath during addition of the acid, and was stored under a helium atmosphere. Studies were performed using the lactate salts of sodium (NaOH, 98.7%, J. T. Baker; 3722-01), potassium (KOH, 85%, Mallinckrodt; 6984), and cesium (CsOH, 99%, Aldrich; 23, 206–8). Preferably the base is between about 50 and 80 percent water. These lactate salts act as both reactants and catalysts in the reaction. Initial semi-batch feed mixtures consisted of lactic acid/alkali lactate mixtures ranging from 0.00 to 0.4233 mole fraction of total lactate as alkali lactate. Total initial feed mass (aqueous lactic acid plus aqueous alkali lactate) ranged from 2.1 to 45.6 grams, with initial water content of 12.00 to 43.31% by weight. Continuous processing has been achieved using feed solutions of up to 88 weight percent by weight lactic acid in water at feed rates of 0.06 to 1.5 ml/min.

Condensed-phase conversion at atmospheric pressure was achieved under a range of reaction conditions. A typical batch temperature ramping program as determined by the controller set point temperature was:

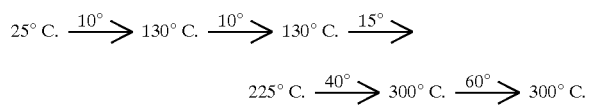

wherein the times are over the arrows. The sample temperature is lower.

Quantifiable yields of 2,3-pentanedione were achieved using maximum reaction temperatures of 200° C. to 360° C., and were also attained using direct ramping to the final reaction temperature. Helium carrier gas flow rates of 25 to approximately 2000 ml/min were used; best results have been achieved at 50 ml/min. Semi-batch reactions (with periodic addition of lactic acid) were performed with total run times of 40 to 555 minutes. In continuous operation, feed addition was started both below 2,3-pentanedione production temperatures (<200° C.), and after the maximum reaction temperature has been reached. Best results in continuous operation have been achieved when feed addition began at approximately 75% of the maximum reaction temperature.

The experimental procedure of Examples 1 to 6 hereinafter involved the following steps for both semibatch and continuous operation:
1. Reactor apparatus 10 (reaction vessel 11, collection traps 12 and 13 and connecting tubing 21, 34 and 35) were tare weighed.

2. A reaction mixture consisting of a predetermined molar ratio of alkali lactate and lactic acid was dispensed into the reaction vessel 11, and the exact mass was recorded.
3. The reactor vessel 11 was assembled, loaded into the heating mantle 22, and carrier gas inlet tube 18 and exhaust tube 21 were attached.
4. Collection trap dewars 31 and 32 were filled with ice and liquid nitrogen, stirring was begun, and carrier gas flow was started.
5. After the carrier gas flow rate was stabilized to approximately 50 ml/min, heating was begun using predetermined ramping or setpoint parameters.
6. For continuous processing only, feed addition was begun when a temperature of approximately 750 of the final setpoint temperature had been reached.
7. Throughout reaction, temperatures of the reactor vessel 11 and heating mantle 22, and quantity of product collecting in the cold traps 12 and 13, were monitored.
8. After reaction was completed and apparatus 10 was cooled, collection traps 12 and 13 connecting tubing 21, 34 and 35, reaction vessel 11 were weighed. Products were weighed and removed separately from each collection trap 12 and 13 for GC analysis. If two phases were present, the product was transferred to a graduated cylinder and diluted with HPLC (high pressure liquid chromatography) grade acetone. If less than 2 grams of product were collected the product was diluted in HPLC water.

Product analysis was performed using a VARIAN Model 3700 (Palo Alto, Calif.) gas chromatograph, connected to a HEWLETT PACKARD Model 3394 (Avondale, Pa.) integrator for determination of product concentrations. The chromatograph used a flame ionization detector and a 4% CARBOWAX 80/100 CARBOPACK B-DA glass column (Supelco, Bellefonte, Pa.). Samples are prepared for injection by a 1:1 mixing with a 10 g/L solution of propanol as an internal standard. Samples which contained only an aqueous phase were mixed directly; two-phase and neat organic samples were diluted in a volume of HPLC-grade acetone or water respectively, adequate to produce a single phase. Dilution sizes were recorded and final concentrations from GC analysis were adjusted accordingly. One microliter samples were injected for analysis. Raw data from the chromatograph, along with feed and product masses, flow rates, and reaction conditions were entered into an EXCEL 6.0 (Microsoft, Redmond, Wash.) spreadsheet program to calculate product yields and selectivities.

Theoretical yield of 2,3-pentanedione from lactic acid/alkali lactate mixtures is calculated from the following:

$$\% \text{ Theoretical Yield} = \frac{\text{g 2, 3-Pentanedione formed}}{\text{mol total lactate initial}} \cdot \frac{2 \text{ mol lactate}}{1 \text{ mol 2, 3-Pentanedione}} \cdot \frac{1 \text{ mol 2, 3-Pentanedione}}{100.12 \text{ g 2, 3-Pentanedione}} \times 100\%$$

Figure 3:
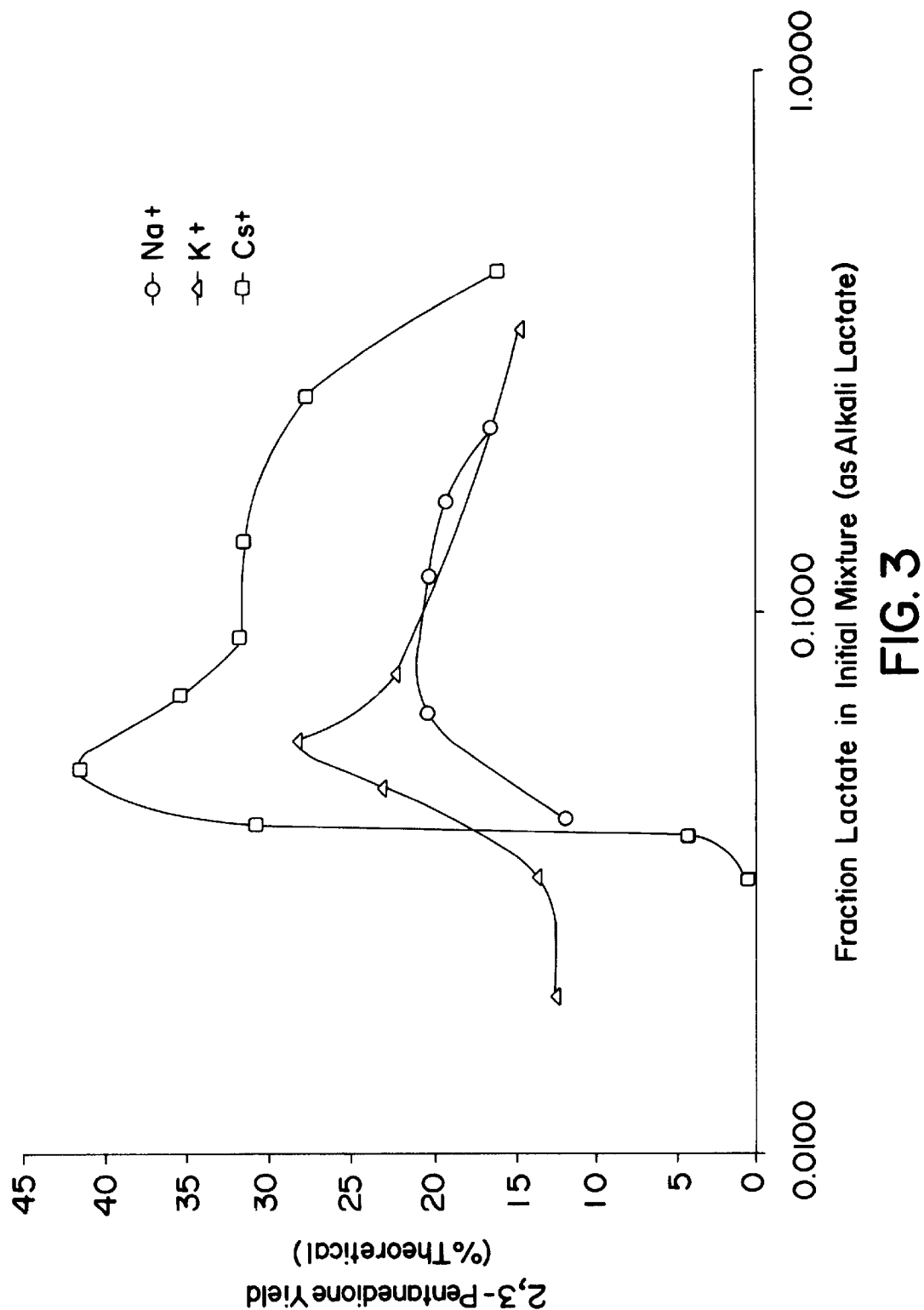
FIG. 3 is a graph showing the yields of 2,3-pentanedione as a function of the ratio of alkali metal lactate to lactic acid in a partially liquid reaction mixture heated to 300° C.
Figure 4:
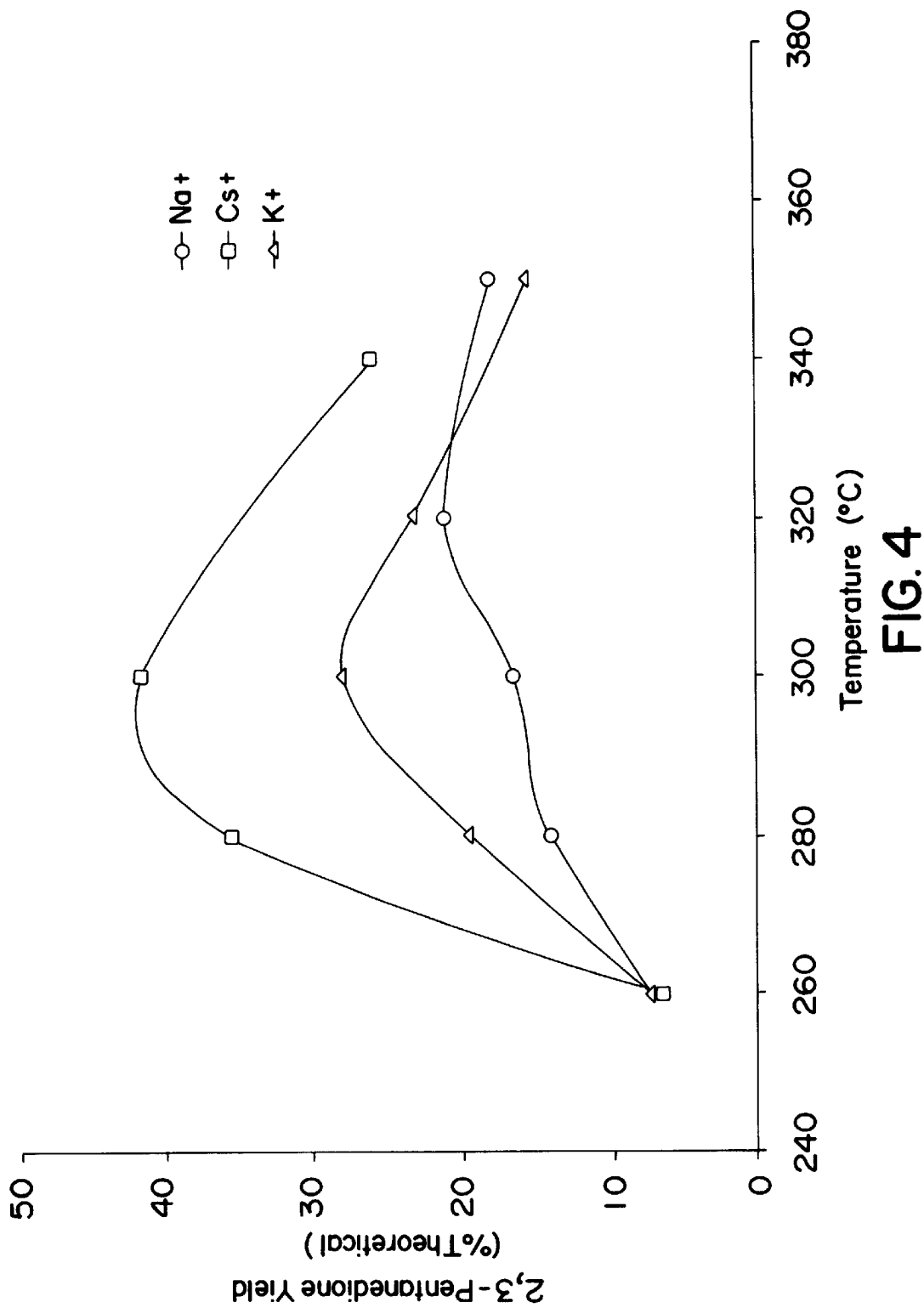
FIG. 4 is a graph showing the yield of 2,3-pentanedione as a function of temperature and the alkali metal lactate used.

Quantifiable yields of 2,3-pentanedione (as percent of theoretical) from semi-batch condensed-phase reaction were achieved using the lactate salts of sodium, potassium, and cesium. For each alkali lactate salt, the yield was a strong function of initial ratio of alkali salt to free acid loaded in the reactor, as illustrated in FIG. 3 for a maximum setpoint temperature of 300° C. Maximum yields of 2,3-pentanedione achieved were 20.47% of theoretical using sodium lactate/lactic acid mixtures, 28.14% of theoretical using potassium lactate/lactic acid mixtures, and 41.50% of theoretical using cesium lactate/lactic acid mixtures. Product yield also depended on maximum reaction temperature;

FIG. 4 shows the yield for alkali lactate salts versus controller setpoint temperature. It should be noted that actual reaction temperature was significantly lower than the controller setpoint temperature because of the cooling effect of product vaporization. Continuous processing demonstrated a yield of 2,3-pentanedione of 20.32% of theoretical from total lactate (initial charge plus lactic acid fed during reaction) over a 8.62 hour experiment for cesium lactate.

EXAMPLE 1

Preparing sodium lactate solution

Sodium lactate solution was formed by adding 16.68 g NaOH pellets slowly to 42.69 g of 88% aqueous lactic acid solution (Purac, Inc., Lincolnshire, Ill.). The resulting sodium lactate solution contained 78.7 percent by weight sodium lactate and 21.3 percent by weight water. This solution was used in preparation of the starting mixtures for condensed-phase reactions.

Condensed-phase formation of 2,3-pentanedione with sodium lactate as catalyst

The sodium lactate solution (2.260 g) was mixed with 11.556 g of 88% aqueous lactic acid solution (Purac) to give an initial reaction mixture containing 12.9 weight percent sodium lactate, 73.6 weight percent lactic acid, and 13.5 weight percent water. This corresponds to about a 7:1 molar ratio of lactic acid to sodium lactate. This mixture was heated with the standard temperature profile for controller temperature to 300° C. as follows:

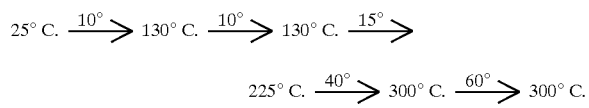

$$25° C. \xrightarrow{10°} 130° C. \xrightarrow{10°} 130° C. \xrightarrow{15°}$$
$$225° C. \xrightarrow{40°} 300° C. \xrightarrow{60°} 300° C.$$

(wherein the times are over the arrows) and held for one hour under helium (50 ml/min) to give a 2,3-pentanedione yield of 1.31 g or 20.3% of the theoretical yield.

EXAMPLE 2

Potassium lactate preparation

Potassium hydroxide as solid pellets (85% KOH) in the amount of 22.086 g was dissolved into 23.344 g water. To this solution was added 34.196 g 88% lactic acid solution to give 79.592 g of a potassium lactate solution containing 53.80 weight percent potassium lactate and 46.20% water.

Condensed-phase formation of 2,3-pentanedione with potassium lactate as catalyst The potassium lactate solution in the amount of 0.914 g, was added to 6.394 g of 88 weight percent solution of lactic acid to give an initial reaction mixture containing 6.73 weight percent potassium lactate, 76.9 weight percent lactic acid, and 16.3 weight percent water. This solution had a lactic acid potassium lactate molar ratio of 16:1. The mixture was heated to 300° C. as in Example 1 and held for one hour under flowing helium (50 ml/min) to give a 2,3-pentanedione yield of 28.2% of theoretical.

EXAMPLE 3

Preparation of cesium lactate

Cesium hydroxide solution (50 weight percent CsOH) in the amount of 20.022 g was mixed with 5.206 g 88 weight percent lactic acid solution to give a CsOH/cesium lactate solution containing 44.78 weight percent cesium lactate, 9.43 weight percent CsOH, and 45.78 weight percent water.

Condensed-phase formation of 2,3-pentanedione with cesium lactate as catalyst

The cesium lactate solution in the amount of 3.88 g was added to 18.02 g 88 weight percent lactic acid solution to give an initial reaction mixture of 21.90 g containing 10.4 weight percent cesium lactate, 71.4 weight percent lactic acid, and 18.2 weight percent water. This solution had a lactic acid:cesium lactate molar ratio of 17:1. The reaction mixture was heated to 300° C. at the heating rates of Example 1 and held for one hour in flowing helium to give a 2,3-pentanedione yield of 3.82 g, or 41.50 of the theoretical yield.

EXAMPLE 4

Continuous, condensed-phase formation of 2,3-pentanedione from lactic acid

An initial reaction mixture of 22.81 g containing 9.6 weight percent cesium lactate, 72.5 weight percent lactic acid, and 17.8 weight percent water was prepared by adding 4.01 g cesium lactate solution as prepared in Example 3 to 18.80 g 88 weight percent lactic acid solution. This mixture contained a 18:1 lactic acid:cesium lactate molar ratio. This mixture was heated to the setpoint temperature of 300° C. When the steady state temperature was reached, 88 weight percent solution of lactic acid was fed to the reactor at a flow rate of 0.06–0.10 ml/min for 230 minutes. A total of 14.2 g of lactic acid solution was fed over the duration of the experiment. The yield of 2,3-pentanedione was 3.96 g or 23.8% of the theoretical yield based on the amount of the lactic acid in the initial mixture plus that added during reaction.

EXAMPLE 5

Continuous addition of water during condensed-phase 2,3-pentanedione formation

An initial reaction mixture of 22.53 g containing 9.8 weight percent cesium lactate 72.2 weight percent lactic acid, and 18.0 weight percent water, made by mixing 4.05 g cesium lactate solution (Example 3) and 18.48 g 88 weight percent lactic acid solution, was heated to 300° C. setpoint temperature using the heating program of Example 1. When the temperature reached 300° C., water was fed to the reaction mixture at 0.1–0.15 ml/min for 45 minutes. A total of 5.8 g of water was added over the course of the experiment. The 2,3-pentanedione yield was 3.28 g or 34.4% of the theoretical yield. The residual product was a clear, amber-color liquid as opposed to the typical black, charred solid from a typical batch experiment; water is expected to reduce dehydration and charring reactions and thus preserve residual lactic acid oligomers for post-reaction hydrolysis and reuse.

EXAMPLE 6

Alternate preparation of initial reaction mixture

Reaction mixture in a 18:1 molar ratio of lactic acid:cesium lactate was prepared by adding 6.33 g of a 50 weight percent aqueous solution of CsOH to 41.76 g of 88 weight percent aqueous solution of lactic acid. The resulting mixture, 48.09 g contained 9.7 weight percent cesium lactate, 72.3 weight percent lactic acid, and 17.7 weight percent water. This mixture has a lactic acid:cesium lactate molar ratio of 18:1.

Continuous condensed-phase 2,3-pentanedione formation

A portion (25.44 g) of the reaction mixture was heated to 200° C. directly, and a 30 weight percent solution of lactic acid was added at a rate of 0.10 ml/min when the temperature reached 200° C. The reaction mixture was then slowly further heated to 230° C. actual solution temperature, which was about 15°–20° C. lower in temperature than Examples 1–6. Addition of 30 weight percent lactic acid solution was continued at a rate of 0.08–0.12 ml/min for a total 405 minutes; a total of 36.22 g of 30 weight percent lactic acid solution was added. The yield of 2,3-pentanedione was 5.89 g, or 35.0% of the theoretical based on total lactate in the starting mixture plus that fed during reaction.

The continuous experiments show that condensed-phase batch production of 2,3-pentanedione can be extended by addition of lactic acid solution during reaction. Continuous addition of lactic acid for up to 8 hours has been achieved at constant temperature, with continuous 2,3-pentanedione production observed. Overall yields of 2,3-pentanedione of 25% have been achieved with CsOH as the catalyst at reaction temperature of 250° C. The residue following the reaction is a viscous liquid, suggesting oligomerization of lactic acid in reactor. Steady state condensed phase conversion with good selectivity to 2,3-pentanedione can be achieved.

As can be seen from the foregoing Examples 1 to 6, significant yields of 2,3-pentanedione from condensed-phase studies was achieved only when both lactic acid and alkali lactate salt are present. There was no diketone formation from lactic acid or alkali lactate alone.

Condensed-phase conversion of lactic acid to 2,3-pentanedione reduces purity requirements of fermentation-derived lactic acid feed, and circumvents processing barriers such as feed vaporization.

It is intended that the foregoing description be only illustrative of the present invention and that the present invention be limited only by the hereinafter appended claims.

We claim:

1. A process for the preparation of 2,3-pentanedione which comprises:
   (a) providing in a reaction vessel a solution of water, an alkali metal lactate and lactic acid in a reaction mixture in the presence of a non-reactive gas;
   (b) heating the reaction mixture in the reaction vessel to a temperature between about 200° and 360° C. to produce 2,3-pentanedione which volatilizes from the reaction mixture along with water;
   (c) removing the volatilized 2,3-pentanedione with water from the reaction vessel; and
   (d) optionally separating the water from the 2,3-pentanedione.

2. The process of claim 1 wherein in step (a) the alkali metal is selected from the group consisting of a potassium, a cesium, potassium, and mixtures thereof.

3. The process of claim 1 wherein the alkali metal is cesium.

4. The process of claim 1 wherein the alkali metal is potassium.

5. The process of claim 1 wherein the alkali metal is sodium.

6. The process of claim 1 wherein the temperature is about 280° to 300° C.

7. The process of claim 1 which is continuous and lactic acid is added to the alkali metal lactate in the reaction vessel.

8. The process of claim 1 which is a batch process.

9. The method of claim 1 wherein in step (c) the volatilized 2,3-pentanedione is cooled to condense the 2,3-pentanedione and water.

10. The process of claim 1 wherein the alkali metal lactate in step (a) is prepared by reacting lactic acid with an aqueous solution of a base of the alkali metal in a stoichiometric amount.

11. The process of claim 10 wherein the lactic acid reacted with the base is food grade.

12. The process of claim 10 wherein the aqueous solution of the base is above about 80% by weight in water.

13. The process of claim 1 wherein a small amount of the water is present in the reaction mixture at the reaction temperatures.

14. The process of claim 1 wherein the temperature is raised in time increments from ambient temperatures.

15. The process of claim 1 wherein the reaction mixture is heated directly to the temperature.

16. The process of claim 1 wherein a mole fraction of alkali metal lactate to lactic acid in the reaction mixture is between about 0.02 to 0.1.

17. The process of claim 1 wherein the temperature is between about 280° and 320° C.

18. The process of claim 1 wherein a mole fraction of alkali metal lactate to lactic acid in the reaction mixture is between about 0.02 to 0.1; and the temperature of the reaction mixture is between about 230° and 260° C.

19. The process of claim 18 wherein the alkali metal is cesium.

20. The process of claim 18 wherein the alkali metal is potassium.

21. The process of claim 18 wherein the alkali metal is sodium.

* * * * *